United States Patent [19]

Engelhardt et al.

[11] Patent Number: 5,668,236
[45] Date of Patent: Sep. 16, 1997

[54] HYDROPHILIC HIGHLY SWELLABLE HYDROGELS

[75] Inventors: Fritz Engelhardt; Ulrich Riegel, both of Frankfurt am Main; Uwe Stüven, Bad Soden; Helmut Klotzsche, Alzenau; Gustav Remmel, Gelnhausen, all of Germany

[73] Assignee: Cassella Aktiengesellschaft, Frankfurt, Germany

[21] Appl. No.: 639,510

[22] Filed: Apr. 29, 1996

Related U.S. Application Data

[63] Continuation of Ser. No. 396,612, Mar. 1, 1995, abandoned.

[30] Foreign Application Priority Data

Mar. 12, 1994 [DE] Germany .................. 44 08 435.8

[51] Int. Cl.⁶ ..................... C08G 69/08; C08G 73/10
[52] U.S. Cl. ..................... 528/310; 528/274; 528/288; 528/303; 525/63; 525/66; 524/523; 524/514; 524/916

[58] Field of Search .................. 528/274, 288, 528/303, 310; 525/63, 66; 524/523, 514, 916

[56] References Cited

U.S. PATENT DOCUMENTS

| 4,075,177 | 2/1978 | Bonnet et al. ............. 260/75 T |
| 4,336,835 | 6/1982 | Taragishi et al. .......... 162/164.3 |
| 5,331,059 | 7/1994 | Engelhardt et al. ........ 525/340 |

*Primary Examiner*—James J. Seidleck
*Assistant Examiner*—Duc Truong
*Attorney, Agent, or Firm*—Connolly & Hutz

[57] ABSTRACT

The present invention relates to a hydrophilic highly swellable hydrogel based on (co)polymerized hydrophilic monomers or based on graft (co)polymers, characterized in that it is post-crosslinked with a polyamidoamine in an aqueous medium.

18 Claims, No Drawings

HYDROPHILIC HIGHLY SWELLABLE HYDROGELS

This application is a continuation of Ser. No. 08/396,612 filed Mar. 4, 1995 now abandoned.

The present invention relates to hydrophilic highly swellable hydrogels post-crosslinked with polyamidoamines in an aqueous medium.

Hydrophilic hydrogels which can be obtained by polymerization of olefinically unsaturated acids, such as, for example, acrylic acid, methacrylic acid, acrylamidopropanesulphonic acid and the like, in the presence of small amounts of poly-olefinically unsaturated compounds are already known and are described, for example, in U.S. Pat. No. 4,057,521, U.S. Pat. No. 4,062,817, U.S. Pat. No. 4,525,527, U.S. Pat. No. 4,286,082, U.S. Pat. No. 4,340,706 and U.S. Pat. No. 4,295,987.

Furthermore, hydrophilic hydrogels which are accessible by grafting copolymerization of olefinically unsaturated acids onto various matrices, such as, for example, polysaccharides, polyalkylene oxides and derivatives thereof, are also known (for example U.S. Pat. No. 5,011,892, U.S. Pat. No. 4,076,663 and U.S. Pat. No. 4,931,497).

The hydrogels mentioned are distinguished by a high absorption capacity for water and aqueous solutions and are therefore preferably used as absorbents in hygiene articles.

It is already known that the properties of these hydrogels can be modified by surface treatment with certain substances. For this purpose, conventional hydrogels, which are dried, ground and if appropriate sieved off, are reacted in powder form with compounds which contain at least two groups which can form covalent bonds with the carboxyl groups of the hydrogels. This crosslinking takes place only on the surface of the gel particles but not inside them.

Such surface crosslinking is described, for example, in EP-A 543 303, mixtures of phosphonic acid diglycidyl esters and other reactive compounds, for example polyamidoamines, being employed as the surface crosslinking agents.

It is also already known to post-crosslink hydrogels in the aqueous gel phase immediately after the polymerization reaction and if appropriate (partial) neutralization of the carboxyl groups with alkali. EP-A 530 438 mentions, for example, ethylene glycol diglycidyl ether, epichlorohydrin and ethylenediamine as crosslinking agents which are suitable for this purpose.

It has now been found that hydrogels having outstanding product properties are obtained if they are post-crosslinked with polyamidoamines.

The present invention thus relates to a hydrophilic highly swellable hydrogel based on (co)polymerized hydrophilic monomers or based on graft (co)polymers, characterized in that it is post-crosslinked with a polyamidoamine in an aqueous medium.

Polyamidoamines are compounds which can be obtained by reaction of an acid component, such as, for example, a dicarboxylic acid or a functional derivative thereof, or an ω-aminocarboxylic acid or lactam thereof, with an amine component, such as, for example, a polyamine, which can also be present as a mixture with alkanolmonoamines, and which can be partly quaternized with epichlorohydrin.

Suitable polyamines contain at least two primary amino groups and preferably at least one secondary and/or tertiary amino group. The ratio between acid and amino component here is preferably chosen such that the resulting polyamidoamine still contains a sufficient number of basic amino groups which can be quaternized with epichlorohydrin.

Polyamidoamines of the type mentioned are known and are described, for example, in DE-A 17 77 824, GB-B 865,727, U.S. Pat. No. 4,075,177, U.S. Pat. No. 4,336,835, DE-A 33 23 732, EP-A 31 899 and EP-A 512 423 and can be prepared by the processes described therein.

Suitable polyamidoamines are, in particular, reaction products of a) saturated or olefinically unsaturated aliphatic $C_3$–$C_{10}$-dicarboxylic acids or functional derivatives thereof or ω-aminocarboxylic acids containing at least 3 C atoms or lactams thereof with b1) aliphatic polyamines which contain at least two primary and at least one further, secondary and/or tertiary amino group, or b2) a mixture of polyamines b1) with c1) polyamines which contain at least one primary and if appropriate at least one secondary amino group and do not fall under the definition b1), it being possible for these polyamines to be used in amounts such that their content of primary amino groups, based on the total amount of primary amino groups, does not exceed 70%, preferably 50%, and in particular 30%, and/or, if appropriate, c2) alkanolmonoamines having 2 to 20 C atoms, preferably 2 to 6 C atoms, and 1 to 3, preferably 1 or 2, OH groups, and in particular having one OH group. Preferably, these alkanolmonoamines have the formula (II) given below.

Preferred possible polyamidoamines are:

1. Reaction products of a) saturated aliphatic $C_3$–$C_{10}$-dicarboxylic acids, such as succinic acid, ($C_1$–$C_6$)-alkyl- or ($C_1$–$C_6$)-alkylenesuccinic acid, glutaric acid, adipic acid, sebacic acid, malonic acid or functional derivatives thereof, such an anhydrides and esters, the three acids mentioned first being preferred, with the mixtures of polyamines with alkanolmonoamines mentioned above under b).

2. Reaction products of those saturated modified dicarboxylic acids or derivatives thereof which are obtained by addition of aliphatic, cycloaliphatic, araliphatic or heterocyclic polyamines which contain at least two amino groups, which are primary and/or secondary, onto α,β-olefinically unsaturated carboxylic acid esters, the alcohol radical of which has 1 to 8, preferably 1 to 3, C atoms, such as ethyl acrylate and methyl methacrylate, and are then reacted with the polyamines mentioned above under $b_1$)/$c_1$), or mixtures thereof, if appropriate mixed with alkanolmonoamines.

3. Reaction products of ω-aminocarboxylic acids containing at least three carbon atoms or lactams thereof, for example 6-aminocaproic acid and 8-aminocaprylic acid or 6-caprolactam and 8-capryllactam, with the mixtures of polyamines with alkanolmonoamines mentioned above under b).

4. Reaction products of olefinically unsaturated dicarboxylic acids, such as maleic acid or fumaric acid, or functional derivatives thereof, such as anhydrides or esters, with the polyamines mentioned above under $b_1$)/$c_1$), or mixtures thereof, if appropriate mixed with alkanolmonoamines.

5. Those reaction products which are based on, in addition to the saturated, aliphatic $C_3$–$C_{10}$-dicarboxylic acids mentioned under 1. and the unsaturated dicarboxylic acids mentioned under 4., also ω-aminocarboxylic acids or lactams thereof of the type mentioned under 3. and, in addition to the polyamines mentioned under b1)

also aliphatic, cycloaliphatic, araliphatic or heterocyclic polyamines and alkanolamines containing at least one primary and, if appropriate, secondary amino group, that is to say, for example, one primary or secondary amino group. Preferred polyamidoamines here are those which are based on, in addition to the polyamines mentioned above under $b_1)/c_1$) or mixtures thereof, if appropriate mixed with alkanolmonoamines, and in addition to the saturated $C_3$–$C_{10}$-dicarboxylic acids, also ω-aminocarboxylic acids or lactams thereof of the type mentioned under 3.

Reaction products of type 1) using ethylenediamine, diethylenetriamine, triethylenetetramine and tetraethylenepentamine as polyamine and 2-aminoethanol as the alkanolmonoamine are particularly preferred.

Possible polyamines b1) and c) are, for example, those of the formula (I)

in which p is zero or an integer from 1 to 6, preferably 1 to 4, $R_1$ is a divalent, preferably non-aromatic hydrocarbon radical having 2 to 18 C atoms, preferably a branched or unbranched alkylene radical having 2 to 10 C atoms, in particular having 2 to 6 C atoms, or a cycloalkylene radical having 5 to 12 C atoms, preferably 6 to 10 C atoms, or an aralkylene radical having 7 to 12 C atoms, preferably 8 to 10 C atoms, and $R_2$ and $R'_2$ independently of one another are H, or one of the two radicals is

wherein $R_1$ has the same meaning as above and $R_3$ and $R_4$ independently of one another are H or ($C_1$–$C_{20}$)-alkyl, preferably ($C_1$–$C_6$)-alkyl, wherein these alkyl radicals can also carry hydroxyl groups.

Polyamines b1) which may be mentioned are, for example, methyl-bis-(3-aminopropyl)-amine, ethyl-bis-(3-aminopropyl)-amine, N-(3-aminopropyl)-tetramethylenediamine, N,N'-bis-(3-aminopropyl)-tetramethylenediamine and polyalkylenepolyamines, such as 1,2-dipropylenetriamine, bis-(3-aminopropyl)-amine, 1,2-tripropylenetetramine and, above all, diethylenetriamine, triethylenetetramine and tetraethylenepentamine.

Polyamines c1) are, for example: ethylenediamine, propylenediamine, 1-amino-3-methylamino-propane, 2-methylpentamethylenediamine, pentamethylenediamine, hexamethylenediamine, trimethylhexamethylenediamine, neopentyldiamine, octamethylenediamine, dioxadodecanediamine, cycloaliphatic diamines, such as 1,2-, 1,3- or 1,4-cyclohexanediamine, 4,4'-methylene-bis-cyclohexylamine, isophoronediamine, menthanediamine, 4,4'-diamino-3,3'-dimethyl-dicyclohexylmethane, 3-aminomethyl-1-(3-aminopropyl-1-methyl)-4-methylcyclohexane, N-methylethylenediamine, N-aminoethylpiperazine and 1,3-bis-aminomethylbenzene.

Suitable alkanolmonoamines are, for example, those of the formula

in which $R_1$ has the above meaning, such as 2-aminoethanol, 1-amino-2-propanol, 3-amino-1-propanol, 2-amino-1-butanol, 4-amino-1-butanol, 5-amino-1-pentanol, 6-amino-1-hexanol and isomers thereof, the hydrocarbon radical of which is branched or which carry the amino group and/or the hydroxyl group on a primary or secondary C atom; and furthermore those which are derived from cyclic hydrocarbon radicals, preferably having 5–7 C atoms.

The ratios of the amounts of the possible components which are to be adhered to for the preparation of suitable polyamidoamines having optimum properties can easily be determined by preliminary experiments.

In general, the molar amount of dicarboxylic acid or functional derivatives thereof with respect to polyamine/alkanolmonoamine is such that the ratio of carboxyl groups to the sum of primary $NH_2$ groups is 1:(0.8–1.4), preferably 1:(0.95–1.1). In the case of mixtures of polyamines and alkanolmonoamines, the ratio of their molar amounts is 0.6:0.4 to 0.99:0.01, preferably 0.8:0.2 to 0.95:0.05.

The preparation of the polyamidoamines can be carried out in the customary manner, for example by heating the corresponding components at temperatures of 125° to 250° C., preferably 140° to 180° C., for several hours with exclusion of oxygen, initially under normal pressure and then under reduced pressure, it being possible to add small amounts of hydrazine hydrate or hydrazides to avoid the polyamines becoming dark in colour. The reaction time depends on the temperatures and pressures used and is in general between 4 and 10 hours.

Polyamidoamines prepared in this manner in general have an average molecular weight $M_n$ (determined by the carboxyl end groups) of at least 500, preferably at least 1000 and in particular 2000 to 20,000; the amine number is usually between 200 and 400, preferably between 250 and 350, mg of KOH/g, and the acid number is between 0 and 50, preferably 10 and 30, mg of KOH/g.

Particularly preferred polyamidoamines are those which have been reacted with epichlorohydrin after their preparation. The ratio of the molar amount of epichlorohydrin to the total of the equivalents of free basic amino groups in the polyamidoamine is 0.6:1 to 4:1, preferably 1:1 to 1.4:1. Free basic amino groups are to be understood as meaning primary, secondary or tertiary amino groups. For the term "equivalents" cf. Pure Appl. Chem. 50 (1978), page 327–338, especially page 337.

Instead of the epichlorohydrin, if appropriate, dichlorohydrin (1,3-dichloro-2-hydroxypropane) can also be employed, preferably 1.0 to 1.4 mol per mole of secondary basic amino groups.

The reaction with epichlorohydrin is carried out, for example, such that the components are reacted at a concentration of the reactants of about 25 to 50%, preferably 35 to 45% and at a temperature between 25° and 95° C., preferably 40° and 75° C., until the viscosity of a 40% strength solution at 25° C. is about 100 to 600, preferably 200 to 400, mPa.s.

Especially preferred polyamidoamines are polyamidoamines which have been reacted with epichlorohydrin and have additionally been subjected to after-treatment with an inorganic base and with a water-soluble organic mono- or polyamine or ammonia or mixtures thereof. The products are appropriately subsequently brought to a pH of 1 to 7 with acid.

The amount of base is 0.1 to 1.0 mol, preferably 0.1 to 0.6 mol, per mole of epichlorohydrin employed. The amount of organic mono- or polyamines is 0.01 to 4, preferably 0.1 to 1, basic amine equivalent per mole of epichlorohydrin.

Inorganic bases which can be employed are, inter alia: alkali metal hydroxides, preferably sodium hydroxide and potassium hydroxide, carbonates, bicarbonates, alkaline earth metal hydroxides, such as calcium hydroxide, and furthermore benzyltrimethylammonium hydroxide or corresponding mixtures.

Possible water-soluble organic mono- or polyamines for the after-reaction according to the invention are preferably compounds of the formulae III or IV

or

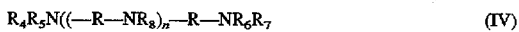

wherein

R is an aliphatic, cycloaliphatic or araliphatic alkylene or hydroxyalkylene radical having 1 to 300 C atoms, which can be interrupted by hetero atoms, such as oxygen and sulphur, and $R_1$, $R_2$, $R_3$, $R_4$, $R_5$, $R_6$ and $R_7$ independently of one another are hydrogen or an aliphatic, cycloaliphatic or araliphatic alkyl or hydroxyalkyl radical having 1 to 20 C atoms, which can be interrupted by hetero atoms, such as oxygen and sulphur, and n is an integer from 0 to 10.

Tertiary monoamines of the formula III are, for example, the following compounds: trimethylamine, triethylamine, tri-n-propylamine, triisopropylamine, tributylamine, N,N-dimethylethylamine, N,N-dimethylisopropylamine, N,N-dimethylcyclohexylamine, benzyldimethylamine, benzyldiethylamine, N-methylmorpholine, N-methylpiperidine, triethanolamine, dimethylethanolamine, diethylethanolamine, diisopropylethanolamine, dibutylethanolamine, methyldiethanolamine, butyldiethanolamine, triisopropanolamine, dimethylisopropanolamine, diethylisopropanolamine, dimethylpropanolamine, diethylpropanolamine, methyldiisopropanolamine, dimethylneopentanolamine and 6-dimethylamino-1-hexanol, secondary monoamines are, for example: dimethylamine, diethylamine, dipropylamine, diisopropylamine, di-n-butylamine, diisobutylamine, di-sec-butylamine, (N-(1-methylpropyl)-2-butanamine, di-n-pentylamine, dihexylamine, di-2-ethylhexylamine, methyl-ethylamine, methyl-propylamine, methyl-butylamine, ethyl-isopropylamine, methyl-isobutylamine, ethyl-butylamine, N-n-propyl-s-butylamine, di-2-methyl-butylamine, N-methyl-cyclohexylamine, N-ethyl-cyclohexylamine, N-butyl-cyclohexylamine, dicyclohexylamine, di-2-methoxyethylamine, diethanolamine, di-n-propanolamine, di-iso-propanolamine, N-methyl-ethanolamine, N-ethyl-ethanolamine, N-methyl-isopropanolamine, cyclohexylethanolamine, morpholine and pyrrolidine, and primary monoamines are, for example: methylamine, ethylamine, propylamine, isopropylamine, n-iso- and sec-butylamine, t-butylamine, n-pentylamine, 3-amino-pentane, 3-methyl-1-butanamine, 2-methyl-2-butanamine, n-hexylamine, 3-amino-3-methylpentane, 2-ethylhexylamine, 3-methyl-1-butanamine, 3-methyl-2-butanamine, 1-methyl-1-butanamine, 2-ethyl-1-butanamine, 2-methoxyethylamine, 2-ethoxyethylamine, 3-methoxypropylamine, 3-ethoxypropylamine, 3-(2-methoxyethoxy)propylamine, cyclopropanamine, cyclopentylamine, cyclohexylamine, 2-methyl-cyclohexylamine, 1- and 2-phenylethylamine, benzylamine, 4-methoxybenzylamine, 1-methyl-3-phenylpropylamine, 2-aminoethanol, 1-amino-2-propanol, 3-amino-1-propanol, 2-amino-1-butanol, 2-amino-3-pentanol, polyhydroxymonoamines, such as 2-amino-2-methyl-1,3-propanediol and 2-amino-2-ethyl-1,3-propanediol, and 2-(2-aminoethoxy)ethanol.

Polyamines of the formula IV are, for example, the following compounds: 1,4-diazabicyclo[2.2.2]octane, N,N,N',N'-tetramethylethanediamine, N,N,N',N'-tetramethyl-1,3-propanediamine, N,N,N',N'-tetramethyl-1,6-hexanediamine, N,N,N',N'-tetramethyldiaminodiethyl ether, N,N,N',N'-pentamethyldiethylenetriamine, ethylenediamine, N,N'-dimethyl-1,2-ethanediamine, N-methyl-1,2-ethanediamine, N-ethyl-1,2-ethanediamine, N,N-diethyl-1,2-ethanediamine, N-(2-hydroxyethyl)-1,2-ethanediamine, 1,2-diaminopropane, 1,3-diaminopropane, 2-hydroxy-1,3-diaminopropane, 3-amino-1-methylaminopropane, N,N-dimethyl-1,3-propanediamine, N,N'-dimethyl-1,3-propanediamine, N,N-diethyl-1,3-propanediamine, N-cyclohexyl-1,3-propanediamine, 2,2-dimethyl-1,3-propanediamine, 1,3-diaminobutane, 1,4-diaminobutane, 1,3-bis(2-hydroxyethylamino)propane, 1,4-bis-methylaminobutane, N,N-diethyl-1,4-pentanediamine, 2-methyl-1,5-pentanediamine, 1,5-pentanediamine, 1,6-diaminohexane, 2,2,4- and 2,4,4-trimethyl-1,6-hexanediamine, 1,2-, 1,3- and 1,4-diaminocyclohexane, menthanediamine, piperazine, 3,5,5-trimethyl-3-aminomethyl-cyclohexylamine, (isophoronediamine), 4,4'-methylene-bis-cyclohexylamine, 4,4'-methylene-bis(2-methyl-cyclohexylamine), bis(2-aminoethyl) ether, 2,2'-bismethylaminodiethyl ether, bis(3-aminopropyl) ether, bis(3-aminopropyl) sulphide, 4,9-dioxadodecane-1,12-diamine, 4,7,10-trioxatridecane-1,13-diamine, 1,3-bisaminomethylbenzene (m-xylylenediamine), TCD diamine (bis(amino-methyl)tricyclodecane), diethylenetriamine, dipropylenetriamine, tetraethylenepentamine, pentaethylenehexamine, tripropylenetetramine, higher polyalkylenepolyamines, methylbis(3-aminopropyl)amine, dihexamethylenetriamine, aminoethylpiperazine, 3-(2-aminoethyl)aminopropylamine, N,N'-bis(3-aminopropyl)ethylenediamine, ethylbis(3-aminopropyl)amine, 2-hydroxyethyl-bis(3-aminopropyl)amine, N-(3-aminopropyl)tetramethylenediamine, N,N'-bis(3-aminopropyl)tetramethylenediamine, 1,3-bis(2-aminoethylamino)propane, 3-(3-diethylaminopropylamino)propylamine, 2,2'-bis(2-aminoethylamino) diethyl ether, 1,6-bis(2-amino-ethylamino)hexane, 1,6-bis(3-aminopropylamino)hexane, bis(6-amino-n-hexyl)amine, polyalkylenepolyamines, polyethyleneimines, polyamidoamines or mixtures thereof. The same polyamidoamines as mentioned and described above are taken as polyamidoamines here.

The after-treatment is carried out, for example, by a procedure in which the solution obtained after the reaction with epichlorohydrin is reacted with an aqueous solution of an inorganic base and with a water-soluble organic mono- or polyamine or ammonia or mixtures thereof at a concentration of the reaction participants of 10 to 50, preferably 15 to 30% and a temperature of between 25° and 95° C., preferably 40° to 75° C., until the viscosity of a 12.5% strength solution at 25° C. is 10 to 200 mPa.s, preferably 15 to 80 mPa.s. The pH is then brought to a pH of 1 to 7, preferably 1.5 to 5, by addition of acid.

The mono- or polyamine can be added immediately after addition of the inorganic base until shortly before the desired viscosity is reached or shortly before the addition of acid. The mono- or polyamine is particularly preferably added in the middle of this reaction period.

In special cases, the mono- or polyamine can also be added before addition of the base. In this case, however, addition of the epichlorohydrin onto the polyamidoamine must have already ended.

Possible halogen-free acids are, above all, sulphuric, phosphoric or acetic acid, anhydrides thereof or also acid salts of these acids.

The especially preferred polyamidoamines which have been reacted with epichlorohydrin and subjected to an after-treatment as described above in general have an average molecular weight $M_n$ of at least 500, preferably at least 1000 and in particular from 1000 to 300,000. The content of organically bonded chlorine is in general between 0.01 and 2.5, preferably between 0.01 and 2, and in particular between 0.01 and 1% by weight. In a 12.5% strength solution, this chlorine content does not exceed values of 0.3% by weight, and is in general between 0.001 and 0.3, preferably between 0.001 and 0.25, and in particular between 0.001 and 0.125% by weight, based on the solution.

The polymers of (co)polymerized hydrophilic monomers or graft (co)polymers on which the hydrogels according to the invention are based are known and are described, for example, in the literature references cited above.

Preferred polymers are those from hydrophilic monomers, such as, for example, acrylic acid, methacrylic acid, $(C_1-C_6)$-alkyl, polyoxy$(C_1-C_3)$alkyl and hydroxy-$(C_1-C_6)$-alkyl esters thereof, crotonic acid, 2-acrylamido-2-methylpropanesulphonic acid and -phosphonic acid, vinylphosphonic acid and esters thereof, vinylamides, vinyl esters and $(C_2-C_6)$-alkenylsulphonic acids or mixtures thereof.

Graft (co)polymers of the monomers mentioned are also preferred, particularly preferably those of acrylic acid and methacrylic acid, it being possible for starch, cellulose, cellulose derivatives, alginates or other biopolymers, hydrophilic polyesters, polyalkylenesulphonic acids, polyvinyl alcohol or polyalkylene oxides to serve as grafting bases.

Suitable polyalkylene oxides have, for example, the formula

wherein $R^1$ and $R^2$ independently of one another are hydrogen, alkyl, alkenyl or aryl, X is hydrogen or methyl and n is an integer from 1 to 10,000.

$R^1$ and $R^2$ are preferably hydrogen, $(C_1-C_6)$-alkyl, $(C_2-C_6)$-alkenyl or phenyl.

In addition, the graft polymers described in U.S. Pat. No. 4,931,497 and U.S. Pat. No. 5,011,892 are also preferred.

The polymers and graft polymers on which the hydrogels according to the invention are based can also already be precrosslinked, suitable crosslinking agents being, for example, methylenebisacrylamide, bisacrylamidoacetic acid, alkenylphosphonic or -phosphinic acid esters, trimethylolpropane tri(meth)acrylate or tetraallyloxyethane.

The hydrogels according to the invention are obtained by reaction of polymers of (co)polymerized hydrophilic monomers or of graft (co)polymers with polyamidoamines in an aqueous medium. It is preferable here to employ the polymers in the form of aqueous gels, which are advantageously comminuted in suitable devices before the reaction. In this case, the reaction with the polyamidoamine is carried out, for example, in a kneader, in which case additional addition of water is not necessary.

The reaction is advantageously carried out at temperatures above 80° C. Temperatures of 80° to 120° C. are preferred.

The polyamidoamines are advantageously employed in amounts such that up to 80 mol % of the carboxyl groups contained in the polymer are neutralized. The polyamidoamines are preferably employed in amounts of 0.2 to 1.0% by weight, based on the starting polymers (calculated as 100% strength goods).

The hydrophilic, highly swellable hydrogels according to the invention are outstandingly suitable as absorbents for water, aqueous solutions and aqueous body fluids and are distinguished by a high absorption capacity, in particular also under a pressure load. They can therefore be used, in particular, in the production of hygiene articles, such as nappies for babies and incontinence pants for adults, bandages, tampons and other absorbent products.

The hydrophilic, highly swellable hydrogels according to the invention can also be used for the preparation of flat and bodied structures having homogeneously water-absorbing properties. For this, the structures mentioned are impregnated by being sprayed, for example, with an aqueous solution of hydrogel and polyamidoamine and are stored at room temperature or elevated temperatures until crosslinking has ended. Suitable flat and bodied structures can consist of naturally occurring fibres and/or synthetic fibres. Preferred structures are absorbent pads of cellulose fluff and mixtures of cellulose fluff and viscose staple and/or polyester.

Both the strength and the absorption capacity of the treated structures can be improved considerably by this use of the hydrogels according to the invention as binders/consolidating agents. Conventional polymers having absorbent properties as a rule are not suitable for preparation of the structures mentioned.

EXAMPLE 1

4780 g of demineralized water are initially introduced into a polyethylene vessel which has a capacity of 10 l and is well insulated by foamed plastic material, 1233 g of sodium bicarbonate are suspended therein and 1994 g of acrylic acid are slowly metered in such that foaming over of the reaction solution is avoided, this cooling to a temperature of about 5°–3° C. The initiators, a redox system consisting of 2.2 g of 2,2′-azobis-amidino-propane dihydrochloride, dissolved in 20 g of demineralized water, 4 g of potassium peroxodisulphate, dissolved in 150 g of demineralized water, and 0.4 g of ascorbic acid, dissolved in 20 g of demineralized water, are added in succession at a temperature of 4° C. and the mixture is stirred thoroughly. The reaction solution is then left to stand, without stirring, a highly viscous gel which readily draws threads being formed due to the polymerization which ensues, during the course of which the temperature rises to about 85° C. This gel is then transferred to a kneader, 2% by weight (based on the acrylic acid) of the solid substance of a commercially available cationic polyamidoamine resin (KYMENE 557H® from Hercules Corp., USA) is added, and the mixture is kneaded homogeneously, comminuted, dried in a stream of air at 180° C., ground and sieved. A water-swellable product having a water absorption capacity of several times its own weight, even under a pressure of 40 g/cm², is obtained.

EXAMPLE 2

A water-soluble polymer gel is prepared by the same procedure as described in Example 1, and is now reacted with 2.5% by weight (based on the acrylic acid) of the active substance of a polyamidoamine of adipic acid, ethylenediamine, ethanolamine and ethylenetriamine, after homogeneous thorough mixing in a kneader. After drying at 180° C., a product which is no longer water-soluble but only swellable and has a water retention capacity of several times its own weight, even under exertion of a pressure of 60 g/cm², is obtained.

EXAMPLE 3

5200 g of demineralized water/ice are initially introduced into a polyethylene vessel which has a capacity of 10 l and is well insulated by foamed plastic material, 695 g of sodium carbonate are suspended therein and 1986 g of acrylic acid are slowly metered in such that foaming over of the reaction solution is avoided, this cooling to a temperature of about 5°–3° C. 25 g of a reaction product, which serves as a graft matrix, of 2 mol of maleic anhydride and 1 mol of an EO/PyO(60/40) block polymer, and 4 g of trimethylolpropane triacrylate and 5 g of a sodium diisooctylsulphosuccinate (REWOPOL V 2133 from Rewo, Steinau) are added. The initiators, a redox system comprising 2.2 g of 2,2'-azobis-amidinopropane dihydrochloride, dissolved in 20 g of demineralized water, 4 g of potassium peroxodisulphate, dissolved in 150 g of demineralized water, and 0.4 g of ascorbic acid, dissolved in 20 g of demineralized water, are added in succession at a temperature of 4° C. and the mixture is stirred thoroughly. The reaction solution is then left to stand, without stirring, a solid gel being formed by the polymerization which ensues, during the course of which the temperature rises to about 85° C., which is then comminuted mechanically. 370 g of 50% strength sodium hydroxide solution are added to 3000 g of the comminuted gel (degree of neutralization of the acrylic acid=73 mol %), the components are thoroughly kneaded twice, 154 g (0.75% by weight, based on the acrylic acid) of a non-quaternized polyamidoamine product, prepared according to Example 6 of EP 0 349 935, which has been diluted to 5% and brought to pH 6.0, are added, and the mixture is again thoroughly kneaded twice and then dried in a thin layer at temperatures above 150° C., ground and sieved. A product which is essentially characterized by the following physical data, all measured in 0.9% strength NaCl, is obtained: extractable contents (1 hour value)=7.8%, absorption under load (AUL) (20 g/cm$^2$)=18.7 g/g, free swell capacity (20 min.)=55 g/g. For comparison:

If the polyamidoamine resin mentioned is not added to the polymer described above before drying, the product, worked up under the same conditions, then has the following values:

extractables=9.9%, AUL=9.6 g/g, FSC=58 g/g.

EXAMPLE 4

4950 g of demineralized water/ice are initially introduced into a polyethylene vessel which has a capacity of 10 l and is well insulated by foamed plastic material, 553 g of sodium bicarbonate are suspended therein and 1986 g of acrylic acid are slowly metered in such that foaming over of the reaction solution is avoided, this cooling to a temperature of about 5°–3° C. 1.5 g of a polyglycol 300-di-maleic acid half-ester, as well as 4.7 g of tetraallyloxyethane, 2.7 g of methylenebisacrylamide, 3.9 g of sorbitan monolaurate and 22 g of urea are added. The initiators, a redox system comprising 1.7 g of 2,2'-azobis-amidinopropane dihydrochloride, dissolved in 20 g of demineralized water, 3.9 g of potassium peroxodisulphate, dissolved in 150 g of demineralized water, and 0.33 g of ascorbic acid, dissolved in 20 g of demineralized water, are added in succession at a temperature of 4° C. and the mixture is stirred thoroughly. The reaction solution is then left to stand, without stirring, a solid gel forming due to the polymerization which ensues, during which the temperature rises to about 85° C., which is then comminuted mechanically, 970 g of 50% strength sodium hydroxide solution are added (degree of neutralization of the acrylic acid=73 mol %), the mixture is thoroughly kneaded twice, 212 g of a commercially available polyamidoamine based on adipic acid, diethylenetriamine, ethylenediamine and ethanolamine, which has been reacted with epichlorohydrin and subjected to an alkali/amine treatment and has been diluted to 5%, are added, and the mixture is again thoroughly kneaded twice and then dried at temperatures above 150° C. in a stream of air, ground and sieved. A product which is essentially characterized by the following physical data, all measured in 0.9% strength NaCl, is obtained: extractable contents (1 hour value)=3.7%, absorption under load (20 g/cm$^2$)=28 g/g, free swell capacity (20 minutes)=45 g/g. For comparison:

If the polyamidoamine resin according to the invention is not added to the polymer described above before the drying operation, then the product worked up under the same conditions has the following values:

extractables=7.9%, AUL=14.5 g/g, FSC=543 g/g.

EXAMPLE 5

3650 g of demineralized water are initially introduced into a 5 l cylindrical wide-necked reaction flask under adiabatic conditions, 500 g of a freshly boiled-up starch solution of 50 g of maize starch and 450 g of demineralized water, 850 g of acrylic acid and 4.0 g of tetraallyloxyethane are dissolved therein and the mixture is brought to 20° C. Nitrogen is passed in to the monomer solution (about 2 l/minute) in order to lower the oxygen content. 64 g of a 4% strength aqueous solution of 2,2'-azobis(amidinopropane) dihydrochloride are added at an $O_2$ content of about 0.8 ppm, 11 g of a 0.75% strength $H_2O_2$ solution are added after passing further $N_2$ in and at an $O_2$ content of 0.08 ppm, and finally 10.5 g of a 0.15% strength ascorbic acid solution are added at an $O_2$ content of about 0.01 ppm. A solid gel is formed due to the polymerization which ensues, during the course of which the temperature rises to about 90° C. and is then comminuted mechanically, 1225 g of 27% strength sodium hydroxide solution are added (degree of neutralization of the acrylic acid=70 mol %), the mixture is thoroughly kneaded twice, 127.5 g of the polyamidoamine according to Example 4, diluted to 5%, are added, and the mixture is again thoroughly kneaded twice and then dried in a thin layer at temperatures above 100° C. ground and, if appropriate, sieved. A product which is essentially characterized by the following physical data, all measured in 0.9% strength NaCl, is obtained: extractable contents (1 hour value)=1.7%, absorption under load (20 g/cm$^2$)=31 g/g, free swell capacity (20 minutes)=49 g/g. For comparison:

If the polyamidoamine resin according to the invention is not added to the polymer described above before the drying operation, then the product worked up under the same conditions has the following values:

extractables=6.9%, AUL=12.5 g/g, FSC=58 g/g.

EXAMPLE 6

A 10% strength aqueous copolymer solution having the monomer composition of 90% by weight of acrylic acid and 10% by weight of acrylic acid and 10% by weight of vinylphosphonic acid, partly neutralized to a pH of 5.5–6.0 with NaOH, having a Fikentscher K value of 187.5 and to which 1.0% by weight of active substance (based on the polyacrylic acid) of a commercially available polyamidoamine based on adipic acid, diethylenetriamine, ethylenediamine and ethanolamine, which has been reacted with epichlorohydrin, has been added was uniformly sprayed onto both sides of an absorbent pad of cellulose fluff (about 6×20×1.5 cm/B×L×H) such that the absorbent pad is charged with 1% of the polymer solid, based on the dry weight of the absorbent pad. After storage at room temperature in air for 24 hours or a corresponding shorter residence time at higher temperatures, the absorbent pads treated in this way were investigated for their strength and absorption capacity against corresponding untreated absorbent pads. The strength was tested by exposing the absorbent pads to a defined stream of air in a special whirling vessel. The constituents which had formed due to the whirling and had been removed from the absorbent pad were suctioned off over a sieve of defined mesh width. The content of undestroyed pad material which remained before the sieve and had not been suctioned off was then determined in %, based on the starting weight.

The absorption capacity was determined as follows: the absorbent pad was soaked in 0.9% strength NaCl solution lying flat on a sheet metal sieve for one minute. The sheet metal sieve was then removed and the pad was allowed to drop for one minute. For this, the test arrangement was inclined about 45°. The increase in weight per gram of absorbent pad was calculated.

An improvement of about 20% in respect of strength and about 10% in respect of absorption capacity was found for the treated absorbent pads in comparison with untreated pads.

EXAMPLE 7

To a 10% strength aqueous solution of an acrylic acid homopolymer which was prepared in a manner known per se, was neutralized to the extent of 70 mol % with NaOH and has a Fikentscher K value of 207 was added 1.5% by weight (based on the acrylic acid) of active substance of a condensation product of 10.43 mol of adipic acid, 6.78 mol of diethylenetriamine, 3.13 mol of ethylenediamine and 1.05 mol of 2-aminoethanol, prepared according to Example 3 of DE 4114657, and, after dilution to a sprayable form, this solution was employed completely analogously to Example 6 as a consolidating agent/binder of non-woven structures of improved absorption capacity.

An improvement of about 10% in respect of strength and about 5% in respect of absorption capacity was found with the treated absorbent pads in comparison with untreated pads.

We claim:

1. A hydrophilic highly swellable hydrogel which comprises polymers prepared by (co)polymerized hydrophilic monomers or graft (co)polymers, that are post-crosslinked with a polyamidoamine in an aqueous medium.

2. The polyamidoamine according to claim 1, wherein said hydrogel is the reaction product of an acid component
   a) saturated or olefinically unsaturated aliphatic $C_3$–$C_{10}$-dicarboxylic acids or functional derivatives thereof or ω-aminocarboxylic acids containing at least about 3 carbon atoms or lactams thereof with the following polyamine component
   b1) aliphatic polyamines which contain at least two primary and at least one further, secondary and/or tertiary amino group, or
   b2) a mixture of polyamines b1) with
   c1) polyamines which contain at least one primary and optionally at least one secondary amino group which does not fall under the definition b1), wherein said polyamines are used in amounts having a content of primary amino groups, based on the total amount of primary amino groups, that does not exceed about 70%, and/or, optionally
   c2) alkanolmonoamines having about 2 to 20 carbon atoms and 1 to 3 OH groups.

3. The hydrogel according to claim 2, wherein said polyamine of component c1) are used in amounts having a content of primary amino groups, based on the total amount of primary amino groups, that does not exceed about 50% and component c2) is alkanolmonoamines having about 2 to about 6 carbon atoms and 1 or 2 OH groups.

4. The hydrogel according to claim 3, wherein the polyamine of component c1) are used in amounts having a content of primary amino groups, based on the total amount of primary amino groups, that does not exceed about 30%.

5. The hydrogel according to claim 2, wherein the acid component a) is selected from the group consisting of succinic acid, ($C_1$–$C_6$)-alkyl succinic acid, ($C_1$–$C_6$)-alkylenesuccinic acid, glutaric acid, adipic acid, sebacic acid, malonic acid, anhydrides, esters and mixtures thereof, and said polyamidoamines are selected from the group consisting of ethylenediamine, diethylenetriamine, triethylenetetramine, tetraethylenepentamine, 2-aminoethanol and mixtures thereof.

6. The hydrogel according to claim 2, wherein the acid component a) is selected from the group consisting of succinic acid, glutaric acid, adipic acid and mixtures thereof, and said polyamidoamine is selected from the group consisting of ethylenediamine, diethylenetriamine, triethylenetetramine, tetraethylenepentamine, 2-aminoethanol and mixtures thereof.

7. A hydrogel according to claim 2, wherein the acid component is selected from the group consisting of 6-aminocaproic acid, 8-aminocaprylic acid, 6-caprolactam, 8-capryllactam, malonic acid, fumaric acid and mixtures thereof.

8. The hydrogel according to claim 2, wherein the polyamines of component b1) and c) are of the formula (I)

in which
p is zero or an integer from 1 to 6,
$R^1$ is a divalent hydrocarbon radical having 2 to 18 carbon atoms, or a cycloalkylene radical having 5 to 12 carbon atoms, cycloalkylene radical having 5 to 12 carbon atoms or an aralkylene radical having 7 to 12 carbon atoms, and $R_2$ and $R'_2$ independently of one another are H, or one of the two radicals is

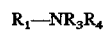

wherein
$R_1$ has the same meaning as above, and $R_3$ and $R_4$ independently of one another are H or a substituted or unsubstituted ($C_1$–$C_{20}$)-alkyl, wherein said substituents are hydroxyl groups.

9. A hydrogel according to claim 8, wherein p is an integer from 1 to 4, $R_1$ is a divalent non-aromatic hydrocarbon radical being a branched or unbranched alkylene radical having 2 to 10 carbon atoms, or a cycloalkylene radical having from 6 to 10 carbon atoms, or aralkylene radical having from about 8 to about 10 carbon atoms and $R_3$ and $R_4$ independently of one another are hydrogen, or substituted or unsubstituted $C_1$–$C_6$-alkyl wherein said substituents are hydroxyl groups.

10. The hydrogel according to claim 2, wherein polyamines of component b1) are selected from the group consisting of methyl-bis(3-aminopropyl)-amine; ethyl-bis-(3-aminopropyl)-amine; N-(3-aminopropyl)-tetramethylenediamine; N,N'-bis-(3-aminopropyl)-tetramethylenediamine; 1,2-dipropylenetriamine, bis-(3-aminopropyl)-amine; 1,2,-tripropylenetetramine diethylenetriamine; triethylenetetramine and tetraethylenepentamine; and said polyamines of component c1) are selected from the group consisting of ethylenediamine; propylenediamine; 1-amino-3-methylamino-propane; 2-methylpentamethylenediamine; pentamethylenediamine; hexamethylenediamine; trimethylhexamethylenediamine; neopentyldiamine; octamethylenediamine; dioxadodecanediamine; 1,2-cyclohexanediamine; 1,3-cyclohexanediamine; 1,4-cyclohexanediamine; 4,4'-methylene-bis-cyclohexylaminel; isophoronediamine; menthanediamine; 4,4'-diamino-3,3'-dimethyl-dicyclohexylmethane; 3-aminomethyl-1-(3-aminopropyl-1-methyl)-4-methylcyclohexane; N-methylethyl-enediamine; N-aminoethylpiperazine; 1,3-bis-amino-methylbenzene; and said alkanolmonoamines of component c2) are of the formula $$H_2N-R_1-OH \qquad (II)$$

in which $R_1$ is a divalent hydrocarbon radical having 2 to 18 carbon atoms, or a cycloalkylene radical having 5 to 12 carbon atoms, or an aralkylene radical having 7 to 12 carbon atoms.

11. The hydrogel according to claim 1, wherein said polyamidoamine is reacted with epichlorohydrin.

12. The hydrogel according to claim 1, wherein said polyamidoamine is reacted with epichlorohydrin and after-treated with an inorganic base and with a water-soluble organic monoamine, polyamine or ammonia or mixtures thereof.

13. The hydrogel according to claim 12, wherein said copolymerized hydrophilic monomers and graft (co) polymers are selected from the group consisting of acrylic acid, methacrylic acid, ($C_1$–$C_4$)-alkyl, polyoxy ($C_1$–$C_3$)-alkyl, hydroxy ($C_1$–$C_6$)-alkyl esters, crotonic acid, 2-acrylamido-2-methylpropanesulphonic acid, 2-acrylamido-2-methylpropanephosphonic acid, vinylphosphonic acid and esters thereof, vinylamides, vinyl esters and ($C_2$–$C_6$)-alkenylsulphonic acids or mixtures thereof, and said bases are selected from the group consisting of starch, cellulose, cellulose derivatives, alginates, hydrophilic polyesters, polyalkylenesulphonic acids, polyvinyl alcohol and polyalkylene oxides.

14. The hydrogel according to claim 1, wherein said (co)polymerized hydrophilic monomers or graft (co) polymers are precrosslinked.

15. An absorbent comprising said hydrogel according to claim 1.

16. The process for the preparation of flat and bodied structures having homogeneously water-absorbing properties comprising impregnating the hydrogel according to claim 1 on to a flat or bodied structure.

17. Flat and bodied structures having homogeneously water-absorbing properties, comprising the hydrogel according to claim 1.

18. A composition comprising flat or bodied structures consisting essentially of naturally occurring fibers or synthetic fibers and the hydrogel according to claim 1.

* * * * *